United States Patent [19]
Park

[11] Patent Number: 5,984,968
[45] Date of Patent: Nov. 16, 1999

[54] REINFORCEMENT FOR AN ORTHOPEDIC IMPLANT

[76] Inventor: Joon B. Park, 1810 Country Club Dr., Coralville, Iowa 52241

[21] Appl. No.: 08/537,112

[22] Filed: Sep. 29, 1995

[51] Int. Cl.[6] .......................................... A61F 2/30
[52] U.S. Cl. .................... 623/18; 623/22; 623/23
[58] Field of Search ..................... 623/18, 23, 22

[56] References Cited

U.S. PATENT DOCUMENTS

| | | | |
|---|---|---|---|
| 3,938,198 | 2/1976 | Kahn et al. | 623/22 |
| 4,038,703 | 8/1977 | Bokros | 623/23 |
| 4,064,567 | 12/1977 | Burstein et al. | 623/18 |
| 4,491,987 | 1/1985 | Park . | |
| 4,735,625 | 4/1988 | Davidson | 623/16 |
| 5,035,714 | 7/1991 | Willert et al. | 623/16 |
| 5,507,814 | 4/1996 | Gilbert et al. | 623/22 |

*Primary Examiner*—Paul B. Prebilic
*Attorney, Agent, or Firm*—Dority & Manning, P.A.

[57] ABSTRACT

An improved method for reinforcing a prosthetic implant and an implant product are provided. The method includes embedding a support structure in a bed of bone cement surrounding the distal end of a prosthetic device. The support structure counteracts hoop-stress imparted to the implant, decreases creep of the bone cement, and further reinforces the bone cement bed. In various embodiments, the support structure can be in the form of a metal coil or in the shape of a wire mesh. Prior to being implanted, the support structure can be precoated with bone cement or can be prefabricated with a prosthetic device.

8 Claims, 4 Drawing Sheets

REINFORCEMENT FOR AN ORTHOPEDIC IMPLANT

BACKGROUND OF THE INVENTION

The present invention generally relates to a method of reinforcing an orthopedic implant and to an implant product. More particularly, the present invention is directed to an improved method of implanting a prosthetic device for counteracting the stresses and strains to which a prosthetic device is typically exposed.

Prosthetic devices are artificial devices used to replace or strengthen a particular part of the body. Such devices can be used in humans or animals to repair or replace diseased or damaged bone, allied tissue associated with the bone, and/or joints associated with the bone. In very general terms, a prosthesis is used to correct or prevent skeletal deformities and to alleviate pain and discomfort caused thereby.

Currently, the most common way to implant a prosthesis is to first prepare a receiving site or cavity in an adjoining bone. A bone cement is placed in the receiving site. A prosthesis is then positioned in the bone cement, while the cement is cured or polymerized.

In most applications, an acrylic bone cement is used. Typically, the bone cement includes an acrylic polymeric powder, such as polymethyl methacrylate (PMMA). The acrylic polymeric powder is premixed with a liquid acrylic monomer system, which may include methyl methacrylate (MMA), resulting in a substance with a dough-like consistency, which is subsequently applied to a bone cavity. After being placed within the cavity, the bone cement is then cured or polymerized and hardened in order to secure the prosthesis within the bone.

Once implanted, a prosthetic device ideally closely assimilates the characteristics of the bone and/or the joint that the device is intended to repair or replace. Further, the implanted prosthetic device should be capable of supporting and withstanding stresses and strains normally imparted to the repaired or replaced bone.

Although the above process for implanting prosthetic devices is generally accepted within the art and has proven to be a successful process for repairing or replacing damaged bones and the like, various problems were still encountered in the past. For example, prosthetic devices were prone to loosen within the bone cavity over time. In particular, most bone cements are neither as strong nor as flexible as bone tissue. Consequently, the bone cement can break away from the prosthesis, can break away from the bone, or can develop stress or fatigue cracks when repeatedly exposed to the normal stress and strains supported by bones.

Due to these problems, attempts have been made to improve the mechanical properties of prosthetic devices and of the cement interface that exists between the device and the bone. For instance, U.S. Pat. No. 4,491,987, filed by the current inventor, which is incorporated herein in its entirety by reference, discloses an improved prosthesis and process for orthopedic implantation of the prosthesis. In that application, a prosthesis is precoated with a polymeric material that is compatible with bone cement. Once implanted, the precoat provides a stronger interfacial bond between the bone cement and the prosthesis.

In U.S. Pat. No. 4,735,625 to Davidson, a prosthesis for reinforced bone cement implantation is disclosed. In one embodiment, the bone cement is reinforced by a mantle or sock formed from a plurality of biocompatible oriented fibers, e.g., polyethylene, carbon, stainless steel or the like. The mantle or sock is sized and shaped to fit over the stem of a typical hip prosthesis. The mantle or sock can be used to form part of a composite precoat by being bonded to the prosthesis prior to implantation.

In another embodiment in Davidson, the fibers can be in the shape of a rectangular mat or in a general cylindrical mantle and embedded in the bone cement. Specifically, it is taught to place the mat or mantle adjacent with the upper portion or proximal end of the stem of the prosthesis.

In U.S. Pat. No. 5,035,714 to Willert, et al., a reinforcement for a bone cement bed is disclosed. The reinforcement includes a grid of crossing members at least some of which are wavy. The reinforcement is provided between the prosthesis and the bone for positioning the prosthesis in place as well as for strengthening the bone cement bed. In particular, the reinforcement is placed at the proximal end of the prosthesis, similar to the embodiment disclosed in Davidson.

The prior art has focused almost exclusively on increasing the fatigue and static fracture resistance of the bone cement bed and on increasing the strength of the interfacial bond between the prosthesis and the bone cement. The present application is directed to further improvements in a bone cement bed and prosthesis combination. Specifically, the present invention is directed to providing a method and implant product that is designed to withstand the radial-stresses and hoop-stresses normally associated with a prosthetic device. As used herein, hoop-stress refers to any circumferential stress or, in other words, any tangential stress that occurs at the periphery of the bone cement bed, at the bone wall, and/or at the outside surface of the prosthetic device.

In particular, hoop-stress can be created when the prosthesis is loaded. More specifically, hoop-stress results between the prosthesis and the surrounding bone cement bed when forces are exerted on or near the end of the prosthesis not embedded within the cement. Hoop-stress can also develop in the bone cement due to shrinkage of the bone cement during polymerization. Conventional bone cement deforms over time, which in turn causes loosening between the prosthetic device and the bone cement bed.

When uncontrolled, hoop-stress can cause the development of microcracks in the bone cement. Further, hoop-stress can cause the prosthesis to separate from the bone cement bed. As such, a need exists for an improved implant product and for a method of implanting a prosthesis that counteracts hoop-stress, decreases shrinkage creep of the bone cement, and further reinforces the bone cement bed.

SUMMARY OF THE INVENTION

The present invention recognizes and addresses further improvements of prior art constructions and methods.

Accordingly, it is an object of the present invention to provide an implant product and an improved method for implanting a prosthesis.

It is another object of the present invention to provide a method of implanting a prosthesis for counteracting the hoop-stress normally associated with prosthetic devices.

Another object of the present invention is to provide an improved method for implanting a prosthesis that decreases the creep of the bone cement.

Still another object of the present invention is to provide an improved implant product in which a support structure is embedded in the bone cement surrounding the distal end of a prosthetic device.

It is another object of the present invention to provide an improved prefabricated implant product in which a precoated wire coil or wire mesh is embedded in a bone cement surrounding the distal end of the prosthetic device.

These and other objects of the present invention are achieved by providing an implant product adapted to replace a predetermined portion of a bone by being affixed to the bone in a bed of bone cement. The implant product includes a prosthetic device for implantation into a prepared area of the body. The prosthetic device includes a stem adapted to be placed within a receiving site formed into a cavity of a bone. The stem has a distal end and a proximal end, wherein a bone cement compatible coating covers at least the distal end of the stem. A support structure is embedded in the bone cement compatible coating. The support structure surrounds the distal end of the stem and is shaped to conform to the contours of the prosthetic device. When the prosthetic device is implanted, the support structure not only reinforces the bone cement bed surrounding the device, but counteracts hoop-stress when the stem is loaded.

In various embodiments, the support structure can be in the form of a metallic coil or a wire mesh. When used to reinforce a hip prosthesis, the support structure can be made from a metal wire having a diameter between about 0.3 millimeters to about 1.0 millimeters.

In an alternative embodiment, the implant product can further include a second support structure embedded within the bone cement compatible coating. The second support structure can surround the proximal end of the stem for further reinforcing the bone cement bed after the prosthetic device has been implanted.

These and other objects are also achieved by providing a method of implanting a prosthesis designed to counteract hoop-stress. The method generally includes the steps of preparing a prosthetic receiving cavity within a bone. The cavity can then be loaded with a predetermined amount of a bone cement. Next, a prosthetic device can be inserted into the bone cement-loaded cavity. According to the present invention, the process also includes the step of embedding a support structure in the bone cement and positioning the support structure such that the support structure encircles at least the distal end of the prosthetic device, between the device and the bone wall.

In the above method, the support structure can include a metallic coil or a wire mesh. The support structure can be made from a metal wire having a diameter between about 0.3 millimeters to about 1.0 millimeters. Further, the support structure can be first precoated with a bone cement compatible material prior to being placed within the receiving cavity. In one embodiment, the bone cement compatible material can be an acrylic polymer composition containing polymethyl methylacrylate.

The method described above can also include the step of placing a second support structure around the prosthetic device. The second support structure can be positioned at the proximal end of the device for further reinforcing the bone cement bed.

These and other objects are further achieved by providing a support structure for placement around the distal end of a prosthesis for counteracting hoop-stress. The support structure can be in the form of a coil made from a metallic material. The coil can be shaped to conform to the prosthesis. A precoat of a bone cement compatible material can cover the coil. Preferably, the precoat has a substantially pore free outer surface for subsequent bonding with a bone cement composition in which the coil is implanted.

The support structure can further include at least two vertical columns enclosing preselected sections of the coil. The columns can be made from a bone cement compatible material and can be spaced at predetermined positions along the coil. In one embodiment, the columns can include alignment tabs projecting inwardly from the interior surface of the coil for contacting and aligning a corresponding prosthesis with the support structure. The alignment tabs can have adjustable lengths for conforming to a corresponding prosthesis.

In another embodiment, the support structure can be completely enclosed within a ring of bone cement compatible material. Preferably, in this embodiment, the ring of bone cement compatible material is adequately perforated for allowing bone cement to flow in between the ring and a corresponding prosthetic device.

Other objects, features and aspects of the present invention are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which.

Repeat use of reference characters in the present specification and drawings is intended to represent same or analogous features or elements of the present invention.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention generally relates to an improved method for implanting a prosthetic device and to an implant product. In particular, the method of the present invention includes placing a support structure within a bone cement bed surrounding the prosthetic device. The support structure is positioned to reside adjacent the distal end of the prosthetic device, between the device and the wall of the receiving cavity. Once installed, the support structure reinforces the implant product, preventing the implant product from being damaged by loads supported by the prosthetic device and, more importantly, hoop-stress to which the bone cement is normally exposed.

The method of the present invention can be applied and used with any prosthetic device that is at least partially embedded into a receiving site or cavity. The receiving site or cavity can be prepared into a bone or into any of its allied tissues. For instance, the method of the present invention can be practiced with any hip prosthesis, shoulder prosthesis, or with any prosthesis that is used to repair or replace a joint.

In general terms, the method of the present invention can include the steps of first preparing a receiving site, canal, or a cavity within a bone that needs to be replaced or repaired. A support structure made in accordance with the present invention and as will be described in more detail hereinafter can then be placed into the bone cavity and positioned at the far end opposite the opening. Bone cement is mixed and inserted into the cavity, surrounding the support structure. As discussed above, the bone cement normally includes a mixture of an acrylic polymeric powder, such as polymethyl methacrylate, and a liquid acrylic monomer, such as a solution of methyl methacrylate.

Immediately after adding the bone cement, the prosthetic device can be positioned within the bone cavity. In particular, the prosthetic device can be positioned so that the distal end of the device is placed adjacent to the support structure embedded within the cement. The bone cement cures and polymerizes for affixing the prosthetic device to the bone.

The method of the present invention and the implant product produced thereby offer many advantages and benefits not before realized by the prior art. First, the implant product of the present invention is designed to reinforce the distal end of the prosthesis for counteracting the hoop-stress created when the prosthesis is loaded. The method of the present invention also decreases the stresses and strains created in the bone cement bed and at the bone-cement interface. Ultimately, a tougher composite structure is formed that is more resistant to the development of microcracks in the cement bed, thus making the cement bed stronger. Adding the support structure to the implant product also decreases creep of the bone cement. Specifically, the support structure itself is not subject to creep and, when included, requires a lesser amount of bone cement to fill the bone cavity, thus reducing polymer shrinkage as well as the exothermic conditions experienced during polymerization and the amount of residual toxic monomer. By decreasing creep in the bone cement, the implant product is subject to less hoop-stress.

Figure 1:
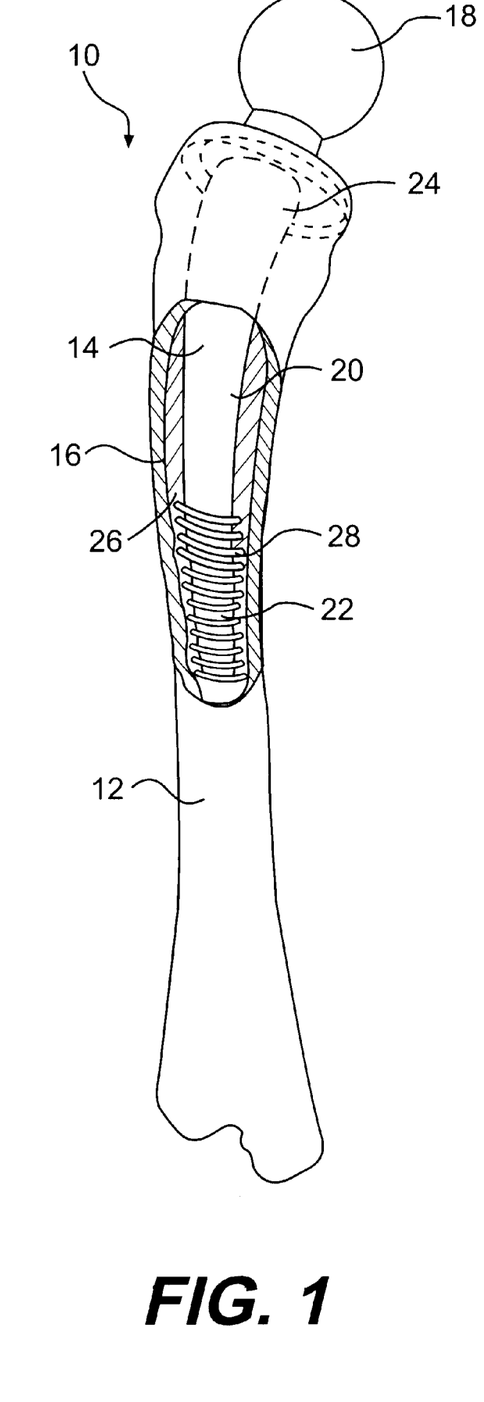
FIG. 1 is a perspective view with cutaway portions of a hip implant, illustrating one embodiment of the present invention.
Figure 2:
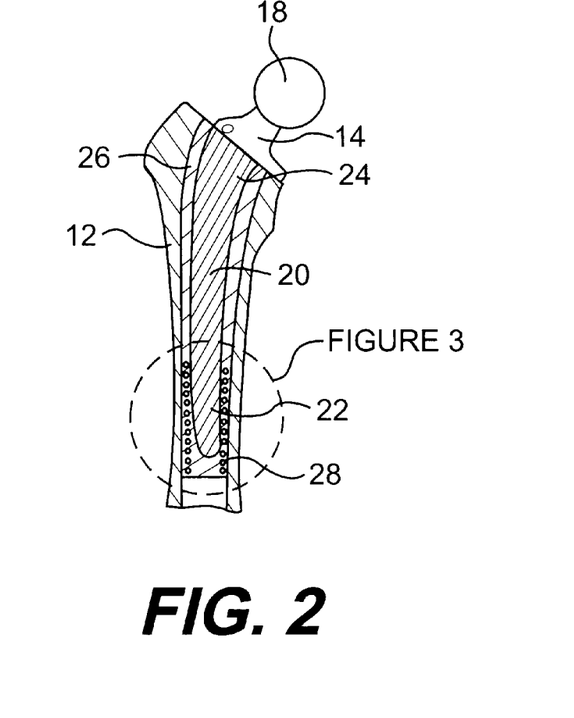
FIG. 2 is a side view of the embodiment illustrated in FIG. 1.
Figure 3:
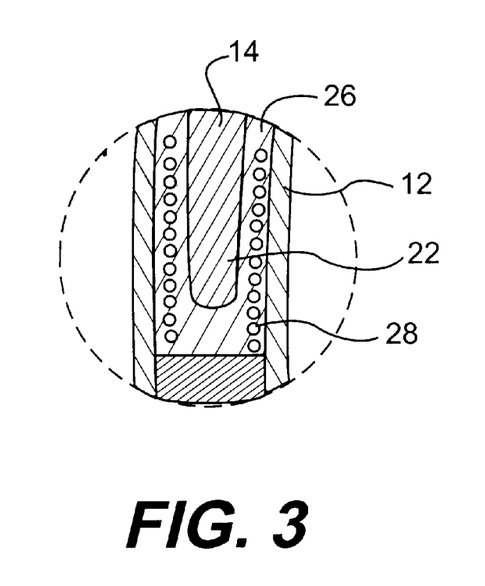
FIG. 3 is an enlarged portion of the drawing in FIG. 2.

Referring to FIGS. 1, 2, and 3, one embodiment of the present invention is illustrated. As shown in FIG. 1, implant product 10 is for repairing and replacing a portion of a bone such as the head of a femur 12, and includes a prosthetic device 14 to be received within a femoral cavity 16. Bone cavity 16 is formed by reaming out a portion of bone 12 as is well known in the art. Prosthetic device 14 includes a head or ball 18 and a stem 20 to be implanted into the bone. Stem 20 has a first or distal end 22 and a second or proximal end 24. In the present invention, stem 20 can be precoated with bone cement or other bone cement compatible material if desired.

As illustrated in FIGS. 1 and 2, stem 20 is surrounded by a bone cement bed 26 within bone cavity 16 for anchoring and securing the prosthetic device within the bone. In accordance with one embodiment of the present invention and as shown in FIGS. 1, 2, and 3, implant product 10 further includes a reinforcing coil or support structure 28 located adjacent distal end 22 of stem 20. As more clearly shown in FIGS. 2 and 3, coil 28 is embedded within bone cement bed 26 between prosthetic device 14 and the bone wall. In this embodiment, coil 28 surrounds and encircles distal end 22 of stem 20. Coil 28 reinforces the bone cement bed, decreases creep in the bone cement, decreases the probability of microcrack development in the cement, creates a tougher composite structure, and, importantly, counteracts the hoop-stress created when the prosthesis is loaded.

The composition and size of reinforcing coil 28 depends upon a number of factors including the size of the prosthetic device, the particular bone being repaired or replaced, and the patient being treated. In general, reinforcing coil 28 can be made from the same material as the prosthetic device and can be designed to conform to the contours of the distal end of the device. In particular, the coil can be made from metallic materials such as a cobalt chromium alloys such as VITALLIUM, molybdenum alloys, titanium alloys, stainless steel, or other metals. Also, high strength polymeric materials can be used alone or in combination with metals. An example of a suitable polymer is poly (p-phenylene terephthalate) or KEVLAR.

Preferably, the support structure of the present invention is made from a metallic or polymeric wire as opposed to being constructed from fibers. As used herein, a wire refers to a continuous structure made from a particular material. Fibers, on the other hand, are slender and greatly elongated filaments. Generally, it has been found that fibers do not provide the strength and rigidity required to counteract hoop-stress when used according to the present invention.

The diameter of the wire used to construct the coil can vary depending upon the particular application. When used to surround the femoral stem portion of a hip prosthesis as illustrated in FIGS. 1–3, the diameter can be between about 0.3 millimeters to about 1.0 millimeters. In one embodiment, coils made from 20 and 24 gauge stainless steel wire were found suitable, which corresponds to a 0.8 millimeter diameter and a 0.5 millimeter diameter respectively. Of course, when repairing bones smaller than a femur, a smaller diameter wire may be preferred.

Figure 1A:
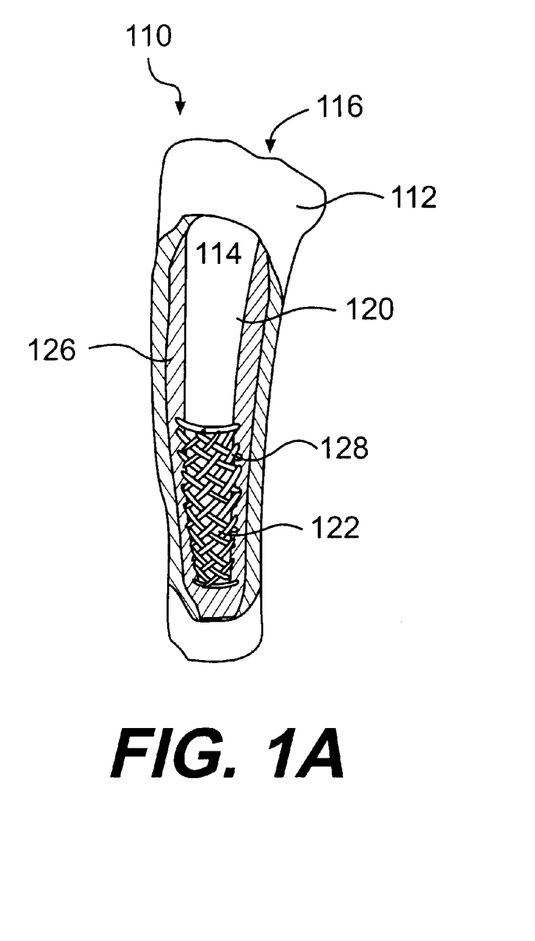
FIG. 1A is a perspective view with cutaway portions of another embodiment of the present invention.

Referring to FIG. 1A, another embodiment of the present invention is illustrated. Included within the figure is an implant product generally 110. Similar to FIG. 1, implant product 110 includes a prosthetic device 114 implanted into a bone 112. In particular, device 114 includes a stem 120 which has been inserted into a bone cavity 116 and anchored therein by a bed of bone cement 126.

As shown in FIG. 1A, positioned at the distal end 122 of prosthetic device 114 is a support structure 128 which, in this embodiment, is in the form of a wire mesh. Specifically, wire mesh 128 can be designed to surround and encircle distal end 122 of stem 120. The mesh can be embedded within the bone cement bed between the prosthetic device and the bone wall.

Wire mesh 128 can be made from the same materials as used to make the wire coil described above. Again, the mesh can be made from the same material as the prosthesis. Preferably, the overlapping strands used to make the mesh are welded or fused together in order to form a strong composite structure.

The support structure made in accordance with the present invention, whether in the shape of a reinforcing coil or a wire mesh, can be procedurally inserted into a bone cavity with a prosthetic device in a number of different ways. For instance, the support structure can be inserted first into a bone cavity followed by the bone cement and prosthetic device or can be inserted into the cavity after first loading the cavity with the bone cement.

Figure 4:
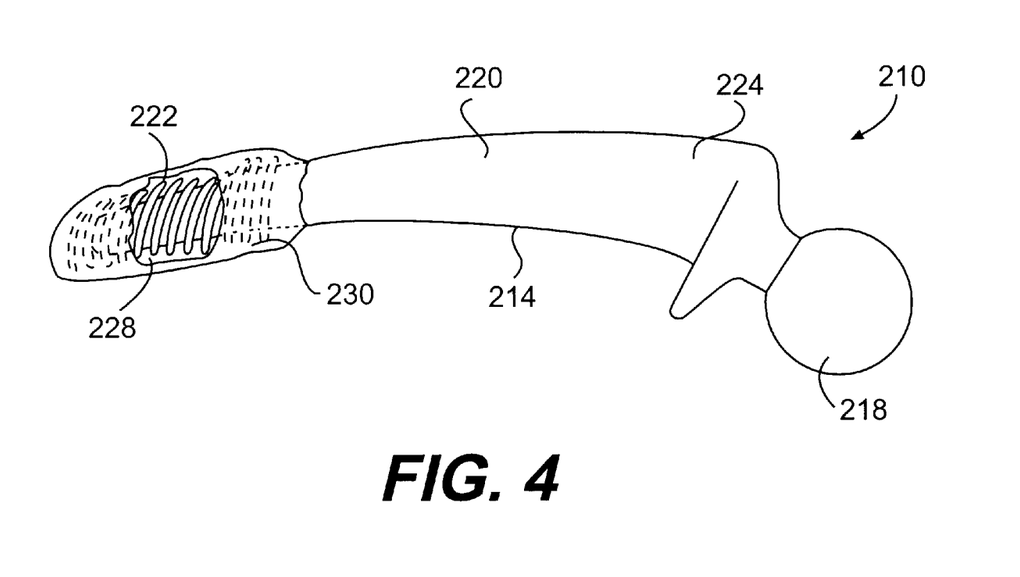
FIG. 4 is a perspective view with cutaway portions of a prefabricated prosthesis made in accordance with one embodiment of the present invention.

Alternatively, the support structure can be included as a part of the prosthetic device as shown in FIG. 4. Referring to the figure, an implant product generally 210 is shown including a prosthetic device 214 having a ball portion 218 and a stem 220. Stem 220 includes a distal end 222 and a proximal end 224. In accordance with the present invention, distal end 222 of stem 220 includes a precoat of bone cement or a bone cement compatible material 230. Embedded within precoat 230 is a support structure 228. In this embodiment, support structure 228 is in form a wire coil as described above.

In producing implant product 210 as shown in FIG. 4, preferably stem 220 of the prosthetic device is first coated with a thin layer of the bone cement material. The coating can be up to about 2 millimeters thick and can cover the entire stem or can be applied just to the distal end. Further, the coating should be smooth and pore free. After coating the stem, support structure 228 can be positioned around the distal end of the stem. Once the support structure is properly positioned, another layer of bone cement or a bone cement compatible material can be applied to the distal end for covering the support structure. Once the support structure is embedded within the layer of bone cement, the cement can be hardened and the finished product can be sterilized for later use.

In this arrangement, the support structure can be embedded in bone cement or a bone cement compatible material surrounding the distal end of the prosthetic device prior to implantation. Before being inserted into a bone cavity, more bone cement can be added to the cavity for forming a layer of cement between the prefabricated implant and the bone wall. By prefabricating the support structure with the prosthetic device, a surgeon implanting the device will not be required to first position the support structure, simplifying the operative procedure by which the present invention may be practiced.

As stated above, the support structure of the present invention can be precoated with bone cement or a bone cement compatible polymer prior to being embedded into a bone cement bed. By precoating the support structure, a stronger interfacial bond may be achieved between the support structure and the cement bed creating a more consolidated and tougher composite implant.

In order to precoat the support structure with a bone cement compatible material, the reinforcing coil or wire mesh can be first pretreated by etching with an acid such as methyl methacrylic acid, sulfuric acid or hydrochloric acid, by roughening with sandpaper, by sand blasting, or in any other similar manner in order to produce, as defined herein, a roughened surface. A roughened surface presents irregularities across the surface and promotes a greater bond strength between the support structure and the bone cement material. Of course, a support structure with a roughened surface can be used in the present invention without being precoated.

After the pretreatment to achieve roughening, the support structure can then be coated with a bone cement compatible material. The coating can be applied by spray painting, dip coating, plasma polymerization or the like. Next, the coating can be cured by exposing the structure to the proper temperature and pressures, which depend upon the material being used as a precoat. A pore free outer surface is preferably formed on the support structure that will readily bond with fresh bone cement. In one preferred method, the precoat can be wiped with a monomer system such as methyl methacrylate prior to being embedded into a bone cement bed, and thus foster bonding between the precoat and the bone cement.

Figure 5:
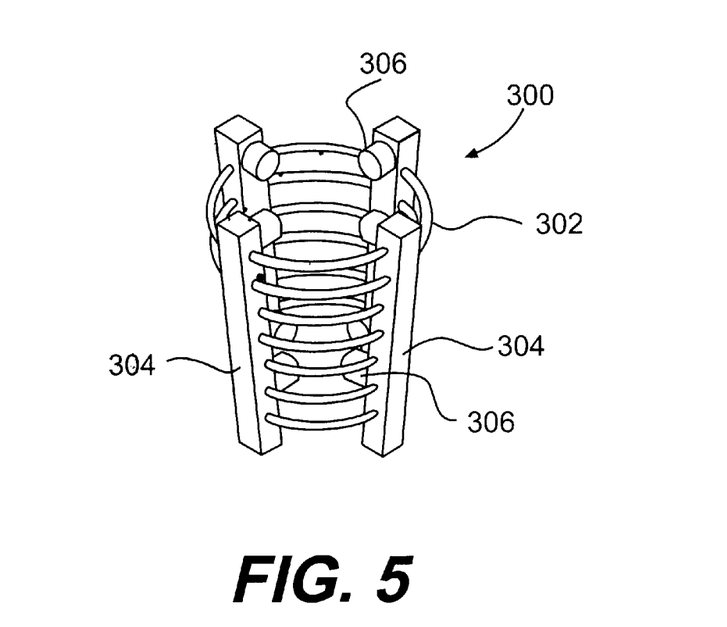
FIG. 5 is a perspective view of a support structure for a prosthesis made in accordance with the present invention.

Referring to FIG. 5, one example of a precoated support structure generally 300 is shown. In this embodiment, support structure 300 includes a wire coil 302. Wire coil 302 is precoated with a bone cement or with a bone cement compatible material. Support structure 300 further includes columns 304 made from bone cement or a bone cement compatible material that enclose at least a portion of coil 302.

Columns 304 provide a dual purpose when used in conjunction with coil 302. First, the columns add rigidity to the support structure, maintaining the coil in a fixed position. Further, the columns include alignment tabs 306 that facilitate placement of the support structure around the distal end of a corresponding prosthetic device. Specifically, support tabs 306 are designed to contact the surface of a prosthetic device, maintaining a proper spacing between the device and the coil. Alignment tabs 306 can include perforated or otherwise weakened portions that can be broken off by a user prior to being implanted. The alignment tabs can thus be adjusted to the correct length corresponding to the prosthetic device being used therewith. Support structure 300 can then be adjusted to be used with prosthetic devices of various sizes and designs.

Another benefit to using columns 304 as shown in the support structure of FIG. 5 is that the columns add support to the coil without interfering with the placement of bone cement between the support structure and the surface of a prosthetic device. As shown in FIG. 5, when the columns are added to the support structure there remains adequate space in between each coil for the passage and flow of bone cement when the support structure is implanted. When a prosthetic device is implanted with support structure 300, it is important that the subsequently applied bone cement provided during the operative procedure fill in all gaps and spaces along the support structure and the prosthetic device for creating a composite structure without interval voids.

Of course, the embodiment illustrated in FIG. 5 represents just one example of a precoated support structure and can be further modified depending upon the circumstances and the particular application. For instance, support structure 300 can include more or less columns 304. Also, alignment tabs 306 can be placed anywhere upon the columns. In one embodiment, coil 302 can be completely enclosed within a ring of bone cement or a bone cement compatible material. In this embodiment, the ring of bone cement must include an adequate number of perforations to allow bone cement to flow in between the support structure and the surface of the prosthetic device when implanted.

Figure 6:
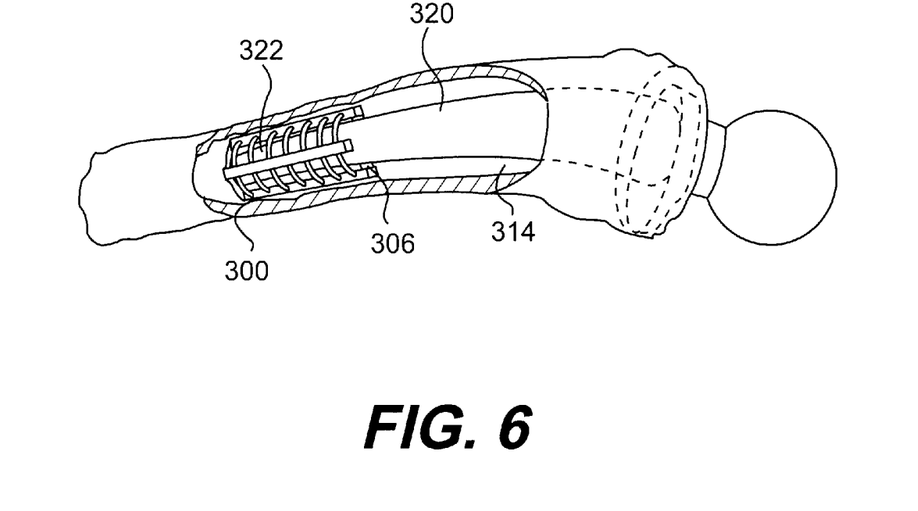
FIG. 6 is a perspective view with cutaway portions of an implanted prosthesis including the support structure illustrated in FIG. 5.

Referring to FIG. 6, support structure 300 is shown embedded into a bone cavity in conjunction with a prosthetic device 314. Prosthetic device 314 includes a stem 320 having a distal end 322. As shown, support structure 300 has been placed around the distal end of the stem. In particular, it is further shown how alignment tabs 306 contact the surface of the prosthetic device causing the support structure to be properly aligned within the bone cavity.

Figure 7:
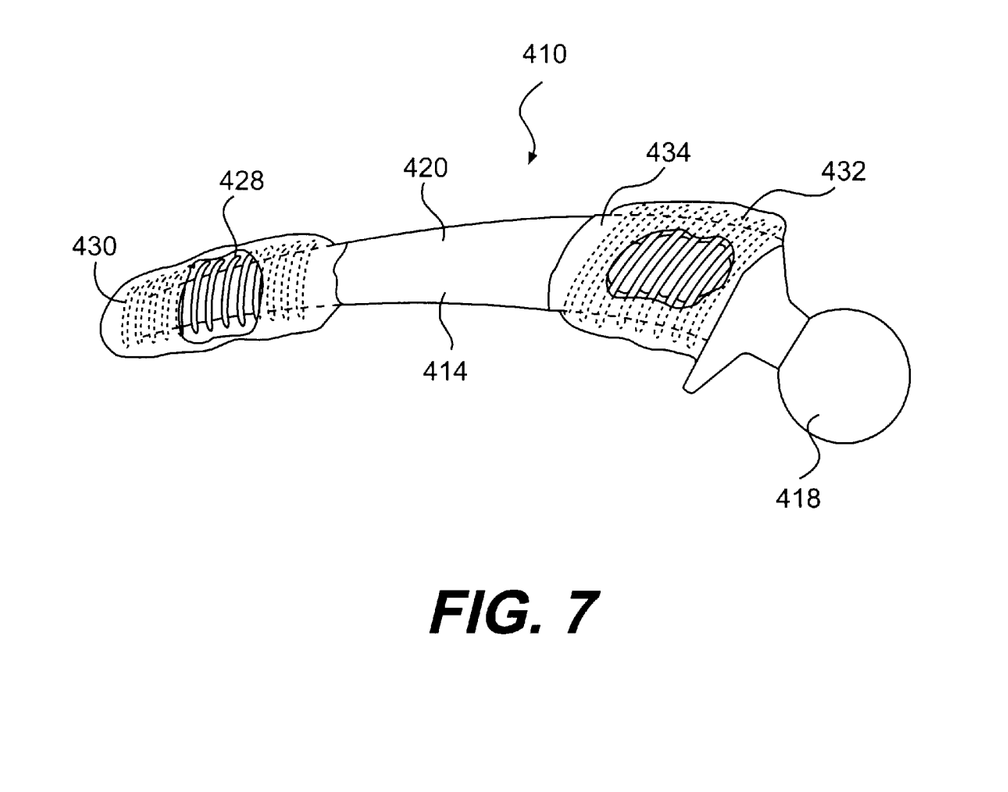
FIG. 7 is a perspective view with cutaway portions of a further embodiment of a prefabricated prosthesis made in accordance with the present invention.

Referring to FIG. 7, another embodiment of a prefabricated implant product generally 410 is shown. Implant product 410 includes a prosthetic device 414 having a stem 420 and a ball or head 418. Similar to FIG. 4, surrounding the distal end of stem 420 is a precoat 430 of polymeric material with a support structure 428 embedded therein. As discussed above, support structure or coil 428 when placed adjacent the distal end of a prosthetic device, reinforces the bone cement bed, reduces creep of the bone cement, and, most importantly, counteracts hoop-stress.

In the embodiment shown in FIG. 7, implant product 410 further includes a support structure 432 embedded within a precoat of polymeric material 434 at the proximal end of stem 420. The addition of support structure 432 at the proximal end of the stem further strengthens and reinforces the bone cement bed providing a dual resistance to stresses and strains imparted to the prosthesis. Of course, a support structure may also be designed to cover the entire length of the prosthesis, but preferably is installed in sections.

In this embodiment, preferably the implant product is prefabricated with the support structures embedded in the bone cement material in order to facilitate later implantation. In constructing the prefabricated product, preferably stem 420 is precoated with bone cement or with a bone cement compatible material. Next, support structures 428 and 432 are positioned at the distal end and proximal end of the stem respectively. Once properly positioned, the support structures are then embedded within an additional layer of bone cement or a bone cement compatible material and the bone cement cured. The finished product is then sterilized for later use.

The present invention may be better understood with reference to the following examples.

EXAMPLE NO. 1

The following tests demonstrate mechanical property changes of a bone cement bed when the bed is reinforced with a support structure in accordance with the present invention.

Coils were first fabricated from 20 and 24 gauge 302/304 stainless steel wire. Specifically, the wire was cut into pieces approximately 60.5 centimeters long and the surface of the pieces were roughened by 20 repeated pulls between 240 grit emery paper held tightly between two fingers. The wires were then coiled on a 1.5 centimeter diameter brass tube by hand. The physical characteristics of the produced coils are summarized in Table 1.

TABLE 1

Some Physical Characteristics of the Coil Specimens

| No. of of Samples | Gauge No. | Wire Dia. (mm) | Wire Length (mm) | ID of Coil (mm) | Height of Coil (mm) | No. Turns |
|---|---|---|---|---|---|---|
| 12 | 24 | 0.5 | 605 | 18.1 | 19.0 | 9 |
| 12 | 20 | 0.8 | 607 | 17.9 | 19.0 | 9 |

The coils were passivated according to the ASTM (American Standards for Testing and Materials) Standard F86. Half the coils were then precoated with polymethyl methacrylate (PMMA) by dipping into a 6.25% by weight dilute solution of the polymer in methyl methacrylate (MMA) monomer liquid resulting in a coating approximately 1.6 microns thick.

After forming the coils, the coils were placed in a metallic mold and embedded in bone cement. The bone cement used was DUZ ALL, obtained from Coralite Dental Products located in Chicago, Ill. and included a self-curing acrylic polymer with a methyl methacrylate monomer liquid. The powder and liquid monomer were combined in a 2 to 1 ratio and mixed thoroughly for 10 seconds. After mixing, the bone cement was injected into the prepared mold with and without the reinforcing coils in the middle of the mold.

After curing, the resulting test specimens were removed from the mold. The specimens were in the shape of a donut with a tapered hole in the middle having a decreasing diameter. The tapered hole corresponds to where the distal end of a prosthetic device would reside. The mold was designed so that the tapering angle was 1.51 degrees. The largest and smallest diameters of the tapered hole were 1.55 centimeters and 1.46 centimeters respectively. The length of the produced specimens was 1.9 centimeters.

The mechanical properties of the cylindrical specimens were then tested and measured by a pushout test until failure took place. Specifically, an MTS hydraulically controlled materials testing machine (MTS Model 812, Minneapolis, Minn.) was used. In particular, a tapered plunger was placed in the tapered hole of the specimens. A load was placed on the plunger such that a constant crosshead speed of 0.60 centimeters per minute was achieved. The plunger was advanced into the specimen until failure occurred. Force-displacement curves were recorded on graph paper during each test. The following results were obtained.

TABLE 2

Summary of the Mechanical Property Measurements

| Specimen Type | No. of Samples | Max. Strain (%) | Max. Load (kN) | Stiffness (GNm/m) | Toughness (Nm/m) |
|---|---|---|---|---|---|
| Control | 19 | 2.6 | 3.70 | 1.73 | 49.33 |
| 24 gauge | 6 | 2.9 | 8.35 | 3.20 | 123.43 |
| 24 ga, precoated | 6 | 3.4 | 9.02 | 3.54 | 157.28 |
| 20 gauge | 6 | 2.9 | 6.08 | 4.15 | 90.28 |
| 20 ga, precoated | 6 | 3.2 | 7.68 | 4.17 | 129.48 |

The maximum load in Table 2 was read from the graphs while the maximum strain was calculated from the maximum displacement, which was converted into hoop-stress using the circumferential length of the specimen at mid-height. The strain was calculated from the mid-section diameter of the hole and the outside diameter and converting the axial displacement from the graph. The stiffness was calculated from the slope of the load-displacement curves. The toughness was calculated from the ultimate strain and load, which represents the amount of energy absorbed by the specimen before fracture.

All measured mechanical properties show the wire coil reinforcement significantly enhanced the strength, fracture strain, stiffness and toughness over the control. The most significant increases were the toughness, indicating that the coil reinforced cement mantle will resist the load much more than the nonreinforced control. Generally, better results were obtained from specimens containing a precoated coil.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An implant product designed to counteract hoop-stress, said implant product comprising:

a prosthetic device for implantation into a prepared area of the body, said prosthetic device including a stem configured to be placed entirely within a receiving site formed in a bone, a distal portion, a middle portion and a proximal portion, said distal proximal portion having a length that is less than half the length of said stem;

a support structure encircling a section of said stem of said prosthetic device, said support structure being made from a wire shaped into a cylindrical configuration generally conforming to the shape of said stem, said support structure having a first end and a second end, said first end of said support structure being placed adjacent to said distal portion of said stem, said support structure extending over said distal portion and terminating adjacent to said middle portion of said stem at said second end; and a mantle made from a bone cement compatible material, said mantle covering at least the distal portion of said stem of said prosthetic device, said mantle enveloping said support structure, whereby said implant product, when implanted with a bone cement composition in situ, will reinforce said bone cement adjacent said distal portion of said stem for counteracting hoop-stress to which said implant product is exposed.

2. An implant product as defined in claim 1, wherein said support structure comprises a coil.

3. An implant product as defined in claim 1, wherein said prosthetic device further comprises a ball attached to said stem, said ball being configured to engage a hip socket.

4. An implant product as defined in claim 1, wherein said bone cement compatible material comprises an acrylic polymer composition.

5. An implant product as defined in claim 1, wherein said support structure is made from a metal wire having a diameter between about 0.3 millimeters to about 1.0 millimeters.

6. An implant product as defined in claim 1, wherein said support structure and said prosthetic device are made from the same material.

7. An implant product as defined in claim 1, further comprising a precoating covering said support structure, said precoating being made from a bone cement compatible material.

8. An implant product as defined in claim 1, wherein said wire is made from a material selected from the group consisting of a metal and a polymer.

* * * * *